United States Patent [19]
Singer et al.

[11] Patent Number: 5,827,660
[45] Date of Patent: Oct. 27, 1998

[54] CAGED FLUOROCHROME-LABELED PROBES AND SUBTRACTION OF AUTOFLOURESCENCE BACKGROUND

[75] Inventors: Robert H. Singer, Shrewsbury; Joan C. Politz, Holden, both of Mass.

[73] Assignee: University of Massachusetts, Boston, Mass.

[21] Appl. No.: 693,786

[22] Filed: Aug. 9, 1996

[51] Int. Cl.[6] ............................. C12Q 1/68; C12Q 1/70; G01N 33/53; G01N 1/00

[52] U.S. Cl. ................................. 435/6; 435/5; 435/7.1; 435/7.2; 435/7.9; 435/287.2; 435/288.7; 422/65; 250/575; 250/461.1; 250/462.1; 250/458.1; 436/63; 436/172; 356/73; 356/318; 356/336; 356/338

[58] Field of Search ........................... 435/6, 5, 7.1–7.9, 435/287.2, 288.7; 422/65; 250/575, 461.1, 462.1, 458.1; 356/73, 318, 336, 338; 436/63, 172

[56] References Cited

U.S. PATENT DOCUMENTS 4,573,796  3/1986  Martin et al. ............................. 356/318
5,514,710  5/1996  Haugland et al. ....................... 514/512

OTHER PUBLICATIONS

Ainger et al., "Transport and Localization of Exogenous Myelin Basic Protein mRNA Microinjected into Oligodenedrocytes," *J. Cell Biol.* 123:431–441 (1993).

Felgner et al., "Enhanced Gene Delivery and Mechanism Studies with a Novel Series of Cationic Lipid Formulations," *J. Biol. Chem.* 269:2550–2561 (1994).

Jacobson et al., "Dynamic Localization of RNase MRP RNA in the Nucleolus Observed by Fluorescent RNA Cytochemistry in Living Cells," *J. Cell Biol.* 131:1649–1658 (1995).

Mitchison, "Polewards Microtubule Flux in the Mitotic Spindle: Evidence from Photoactivation of Fluorescence," *J. Cell Biol.* 109:637–652 (1989).

Politz et al., "Characterization of hybridization between synthetic oligodeoxynucleotides and RNA in living cells," *Nucleic Acids Res.* 23:4946–4953 (1995).

Wang et al., "Localization of pre–messenger RNA at discrete nuclear sites," *Proc. Natl. Acad. Sci.* 88:7391–7395 (1991).

*Primary Examiner*—W. Gary Jones
*Assistant Examiner*—Dianne Rees
*Attorney, Agent, or Firm*—Fish & Richardson P.C.

[57] ABSTRACT

Disclosed are methods for removing autofluorescence background from microscopic images or from flow cytometer measurements. The microscopic images can be fluorescent in situ hybridization images or images of living cells. The methods involve the steps of: (1) detecting fluorescence from a cell before "uncaging" a caged fluorochrome label on a probe; (2) uncaging the fluorochrome; (3) detecting fluorescence from the cell; and (4) subtracting fluorescence detected before uncaging from fluorescence detected after uncaging. Also disclosed is a method for tracking the movement of a target molecule in a living cell. Also disclosed is a fluorochrome-uncaging flow cytometer. The fluorochrome-uncaging flow cytometer includes a first fluorescence excitation light beam, an uncaging light beam, a second fluorescence excitation light beam, an electronic data system, a first photodetector operably linked to the electronic data system, and a second photodetector operably linked to the electronic data system.

20 Claims, 3 Drawing Sheets

CAGED FLUOROCHROME-LABELED PROBES AND SUBTRACTION OF AUTOFLOURESCENCE BACKGROUND

STATEMENT AS TO FEDERALLY SPONSORED RESEARCH

Work on this invention was supported, in part, with funds from the United States government (NIH grant nos. F32AR0836101 and HD18066). The government therefore has certain rights in the invention.

FIELD OF THE UNVENTION

The invention relates to cell biology, in situ hybridization, fluorescence microscopy, flow cytometry, and digital imaging.

BACKGROUND OF THE INVENTION

Fluorochrome moieties have been widely used as detectable labels on molecular probes in fluorescence microscopy. For example, fluorochrome-labeled nucleic acid probes are commonly used in in situ hybridization. Fluorochrome-labeled markers are also used in flow cytometry. For example, a fluorochrome-labeled CD4 ligand can be used as a cell surface marker allowing lymphocytes to be counted, sorted, or both.

When fluorochrome-labeled probes are used in fluorescence microscopy or flow cytometry, the minimum number of bound probe molecules that can be detected is often an issue. In general, the sensitivity of fluorescent probe detection in living cells is limited by autofluorescence "noise" rather than the absolute sensitivity of the detection apparatus. For example, most commercial flow cytometers can detect a few hundred molecules of fluorescein. That does not mean, however, that they can detect a few hundred molecules of fluorescein associated with a living cell. Autofluorescence in a living cell can be equivalent to tens of thousands of fluorescein molecules.

Cells typically contain flavins and other biochemical compounds that fluoresce in response to wavelengths used to excite fluorochrome labels. The excitation and emission spectra of autofluorescence in several cell types are close to the spectrum of riboflavin. The amount of autofluorescence depends on excitation wavelength, which depends on which fluorochrome label is used. Fluorescein, typically excited at 488 nm, is notably associated with autofluorescence problems. Relatively less autofluorescence occurs with excitatory wavelengths above 515 nm, which are normally used for fluorochromes such as TRITC and Texas red. To be detectable in practice, a probe's fluorescence signal must be detectable above the autofluorescence noise.

In a cell population, autofluorescence varies from cell to cell, in a normal distribution. A flow cytometer can produce a fluorescence frequency distribution. If a substantial fraction of cells in a population has bound probe and a substantial fraction does not, the resulting fluorescence frequency distribution is bimodal, typically with some overlap of the peaks. Thus, in fluorescence-based flow cytometry, cells have been scored according to cut-off values based on statistics and probability. Such probabilistic methodology inevitably involves a certain level of imprecision.

In fluorescence microscopy on individual living cells, as well as in flow cytometry, autofluorescence has been an obstacle. A hybridized fluorescent probe must be distinguished against autofluorescence background noise. Autofluorescence is particularly problematic in attempts to monitor the location of, or track the movement of, individual molecules such as mRNAs in living cells.

In situ hybridization studies on fixed cells have shown that some mRNAs are concentrated in discrete regions within the cell (Singer, Curr. Biol. 3:719–721 (1993)). For example, some maternal mRNAs become localized to particular subcellular regions during embryogenesis (Gavis et al., Cell 71:301–313 (1992); Berleth et al., EMBO J. 7:1749–1756 (1988); Kloc et al., Science 265:1101–1103 (1994). In some somatic cells, β-actin mRNA is found localized to the leading edge of fibroblast lamellipodia (Lawrence et al., Cell 45:407–415 (1986). In such studies, however, the nature of RNA movement with cells was surmised after fixation of the cells.

Hybridization of antisense oligonucleotides to mRNA in living cells has been directly demonstrated (Politz et al., Nucl. Acids. Res. 23:4946–4953 (1995). Even there, however, cells were fixed before data were obtained. Messenger RNA has been fluorescently-labeled, microinjected into living cells, and then observed in the living cells (Jacobson et al., J. Cell Biol. 131:1649–1658 (1995).

Autofluorescence presents signal-to-noise ratiorelated limitations in fluorescent in situ hybridization performed on fixed cells, as well as fluorescence microscopy performed on living cells. In fixed cells, the autofluorescence background is predominantly associated with proteins, rather than small molecules such as riboflavin, which tend to be removed during fixation. The intensity of autofluorescence varies from cell to cell. It is also spatially variable within cells. Commonly, fluorescence background is measured in a similar cell type and an average autofluorescence/pixel value is calculated and subtracted from total autofluorescence/pixel measured in the cell.

SUMMARY OF THE INVENTION

In general, the invention relates to removing autofluorescence background from microscopic images or from flow cytometer measurements. The invention has several aspects, summarized separately, below. Some aspects of the invention are methods for removing autofluorescence background. One aspect of the invention is a fluorochrome-uncaging flow cytometer. Methods according to the invention involve the basic steps of: (1) detecting fluorescence from a cell before "uncaging" a caged fluorochrome label on a probe; (2) uncaging the fluorochrome; (3) detecting fluorescence from the cell after uncaging the fluorochrome; and (4) subtracting fluorescence detected before uncaging from fluorescence detected after uncaging.

In a first aspect, the invention features a method for removing autofluorescence background from a fluorescent in situ hybridization image of cellular material. The method includes the steps of: (a) fixing the cellular material with a fixative that retains and preserves a target molecule, if present; (b) contacting the cellular material with a caged fluorochrome-labeled molecular probe that binds specifically to the target molecule; (c) interrogating the cellular material a first time to obtain a first digitized image containing an autofluorescence background; (d) uncaging the fluorochrome label on the molecular probe; (e) interrogating the cell a second time to obtain a second digitized image containing (1) a fluorescence signal from the uncaged fluorochrome, and (2) the autofluorescence background; and (f) digitally subtracting the first digitized image from the second digitized image. Preferably, the subtraction is on a pixel-by-pixel basis. Typically the cellular material includes a cell nucleus. Typically, the target molecule is a nucleic acid and the molecular probe is an oligonucleotide. Preferred caged fluorochromes include bis-caged carboxyfluorescein, Rhodamine Green™ bis-(((4,5-dimethoxy-2-nitrobenzyl) oxy)carbonyl)-caged succinimidyl ester, and Rhodamine Green™ bis-(((4,5-dimethoxy-2nitrobenzyl)oxy)carbonyl)-caged sulfo-succinimidyl ester.

In a second aspect, the invention features a method for tracking a target molecule in a living cell. The method includes the steps of: (a) obtaining a caged fluorochrome-labeled molecular probe that binds specifically to the target molecule; (b) introducing the molecular probe into a living cell; (c) interrogating the living cell a first time to obtain a first digitized image containing an autofluorescence background; (d) uncaging the fluorochrome in a portion of the living cell; (e) interrogating the cell a second time to obtain a second digitized image containing (1) a fluorescence signal from the uncaged fluorochrome, and (2) the autofluorescence background; (f) digitally subtracting the first digitized image from the second digitized image; (g) repeating steps (c)–(f) at selected time intervals; and (h) comparing the substantially autofluorescence-free digitized images obtained at the selected time intervals to detect a slowly-moving fluorescence signal, as an indication of the target molecule. Preferably, the subtraction is on a pixel-by-pixel basis.

The portion of the cell can be the entire cell or less than the entire cell. Preferably, the fluorochrome is uncaged by means of a laser beam having a diameter from about 0.1 $\mu$m to about 2.0 $\mu$m. More preferably, the uncaging laser beam has a diameter of about 0.5 $\mu$m. Preferred caged fluorochromes include bis-caged carboxyfluorescein, Rhodamine Green™ bis-(((4,5-dimethoxy-2-nitrobenzyl)oxy)carbonyl) -caged succinimidyl ester, and Rhodamine Green™ bis-((  (4,5-dimethoxy-2-nitrobenzyl)oxy)carbonyl)-caged sulfo-succinimidyl ester.

In a third aspect, the invention features a fluorochrome-uncaging flow cytometer. The flow cytometer includes an electronic data system and a flow system. The flow system includes: (a) a core; (b) a first fluorescence excitation light beam focused on a first fluorescence interrogation point in the core; (c) a first collection lens situated to collect fluorescence emitted from the first fluorescence interrogation point and focus the fluorescence onto a first photodetector operably linked to the data system; (d) an uncaging light beam focused on an uncaging point in the core, with the uncaging point being downstream from said first interrogation point; (e) a second fluorescence excitation light beam focused on a second fluorescence interrogation point in the core; (f) a second collection lens situated to collect fluorescence emitted from the second fluorescence interrogation point and focus the fluorescence onto a second photodetector operably linked to the data system. Preferably, the first and second fluorescence excitation light beams are lasers. Preferably, the uncaging light beam is an ultraviolet laser.

In a fourth aspect, the invention features a non-probabilistic method for fluorescence-based flow cytometry of cells in a cell population contacted with a caged fluorochrome-labeled molecular probe that binds specifically to a target molecule. The method includes the following steps: (a) moving the cells single file into a core in a fluorochrome-uncaging flow cytometer; (b) moving a first cell through an excitation light beam focused on a first interrogation point in the core, in a first interrogation; (b) collecting fluorescence emitted from the first cell in response to the first interrogation, and focusing the collected fluorescence onto a first photodetector operably linked to an electronic data system; (c) storing an autofluorescence background value from the first photodetector, in the electronic data system; (d) moving the first cell through an uncaging light beam focused on an uncaging point in the core, with the uncaging point being downstream from the first interrogation point; (e) moving the first cell through a second excitation light beam focused on a second interrogation point, in a second interrogation; (f) collecting fluorescence emitted from the first cell in response to the second interrogation, and focusing the collected fluorescence onto a second photodetector operably linked to an electronic data system; (g) storing an autofluorescence background-plus-signal value from the second photodetector, in the electronic data system; and (h) electronically subtracting the autofluorescence background value from the autofluorescence background-plus-signal value, thereby obtaining a fluorescence signal value. Typically, the excitation light beams focused on the interrogation points are lasers. Typically, the uncaging light beam is an ultraviolet laser.

As used herein, "autofluorescence" means fluorescence emitted from a living or fixed cell during interrogation, which fluorescence is not from a selected fluorochrome associated with a molecular probe.

As used herein, "to bind specifically" (applied to a labeled molecular probe) means to bind to a target molecule without substantial binding to non-target molecules.

As used herein, "caged cell" means a cell containing a caged probe.

As used herein, "caged fluorochrome" means a nonfluorescent chemical compound that becomes fluorescent upon photolysis of a photolabile fluorescence-inhibiting moiety.

As used herein, "caged probe" means a probe bearing a caged fluorochrome.

As used herein, "cellular material" means a thin section of tissue, an individual cell, an isolated cell nucleus or cell organelle, a virus associated with a cell, a chromosome, or any part of a cell.

As used herein, "flow cytometry" means a process in which measurements of physical and/or chemical characteristics of cells are made while the cells pass, in single file, through the measuring apparatus in a fluid stream.

As used herein, "fluorescence-based flow cytometry" means flow cytometry in which the physical and/or chemical characteristics are measured indirectly by means of an fluorochrome-labeled molecular probe that binds with specificity to a target molecule.

As used herein, "fluorochrome-uncaging flow cytometer" means a flow cytometer whose flow chamber includes a first fluorescence excitation light beam, an uncaging light beam, a second fluorescence excitation light beam, an electronic data system, a first photodetector operably linked to the electronic data system, and a second photodetector operably linked to the electronic data system.

As used herein, "interrogating a cell" means exposing a cell to light at a wavelength that is excitatory for a selected fluorochrome, and detecting a fluorescence emission, if present, from the selected fluorochrome.

As used herein, "slowly-moving fluorescence signal" means a fluorescence signal represented by a pixel or a group of contiguous pixels that translocates in a living cell at a velocity between about 1 and about 100 microns per minute.

As used herein, "sorting" cells means counting cells scored above or below one or more cutoff values for one or more parameters, or physically separating cells scored above or below one or more cutoff values for one or more parameters, or both, by flow cytometry.

As used herein, "substantial binding" to non-target molecules means a level of binding that results in a spurious signal level sufficient to obscure or confuse signals from target molecules.

As used herein, "target molecule" means an intracellular molecule to which a molecular probe binds with specificity.

As used herein, "tracking" means detecting the transit of a target molecule from one point to another point, within an individual living cell, over time.

As used herein, "uncaged probe" means a probe bearing an uncaged fluorochrome label.

As used herein, "uncaged cell" means a cell containing an uncaged probe.

As used herein, "uncaging" a fluorochrome means rendering a previously non-fluorescent compound fluorescent, i.e., activating a fluorochrome, by photolysis of a photolabile caging moiety. This is typically done with a flash of light from a UV laser.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

DETAILED DESCRIPTION

Figure 1A:
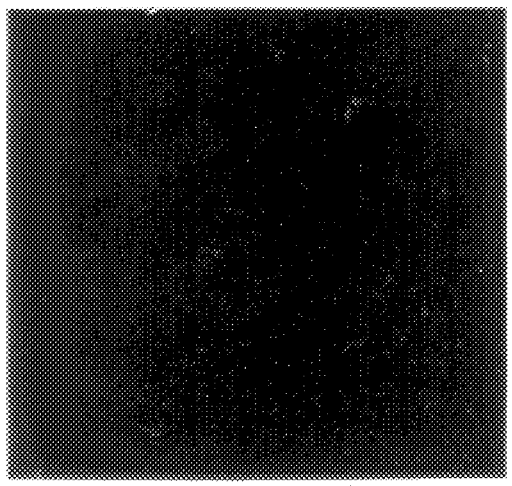
FIG. 1A is a digital image of a living cell before uncaging of a caged fluorochrome-labeled oligo-dT probe, after the autofluorescence background has been electronically subtracted.

Some aspects of the invention are methods for removing autofluorescence background from microscopic images or from flow cytometer measurements. One aspect of the invention is a fluorochrome-uncaging flow cytometer. Each method according to the invention involves the use of a molecular probe, e.g., an oligonucleotide, labeled with a "caged" fluorochrome. Each method involves the steps of: (1) detecting fluorescence from a cell before "uncaging" a caged fluorochrome label on a molecular probe; (2) uncaging the fluorochrome; (3) detecting fluorescence from the cell after uncaging the fluorochrome; and (4) subtracting fluorescence detected before uncaging from fluorescence detected after uncaging. Operation of the fluorochrome-uncaging flow cytometer involves these method steps.

Removing autofluorescence background from a fluorescent in situ hybridization image of cellular material is useful for increasing the signal-to-noise ratio. This significantly increases the effective sensitivity of fluorescent in situ hybridization.

Tracking the movement of individual molecules in living cells can be used to elucidate normal molecular biological processes and to diagnose abnormal processes.

The improved flow cytometer and the flow cytometry methods of this invention can be used in the practice of medicine. For example, it can be used in clinical hematology and clinical immunology for various tasks involving blood cell counting, classification, or separation. The fluorochrome-uncaging flow cytometer and the flow cytometry methods of this invention can also be used as laboratory tools in basic biomedical research.

Probe and Target Molecules

When the target molecule is to be detected in a fixed cell by fluorescent in situ hybridization, the probe can be any molecule that binds specifically to the target molecule, provided that it can be labeled with a caged fluorochrome. When the target molecule is in a living cell, an additional requirement is that the probe must be capable of introduction into a living cell. When the target molecule is on the cell surface, the probe need not be able to cross the cytoplasmic membrane, and inability to do so is preferable. Inability to cross the cytoplasmic membrane minimizes the likelihood of spurious signals from cell surface-directed probes trapped inside cells. Exemplary probe molecules are antisense oligonucleotides, receptor protein-specific ligands, and receptor protein-specific antibodies.

Preferably, the probe is relatively small with respect to the target molecule, when the probe is used to track the movement of the target molecule in a single cell. This minimizes artifacts in the target molecule's intracellular movement caused by the presence of the bound probe.

The target molecule can be any macromolecule for which a probe labeled with a caged fluorochrome is available. For example, a target molecule can a receptor protein, which is nuclear or cytoplasmic, and is soluble or integrated in a membrane. Alternatively, the target molecule can be a nucleic acid ("target nucleic acid"), which is DNA or RNA, and is nuclear or cytoplasmic. Examples of target nucleic acids include an mRNA native to the interrogated cell, a pre-mRNA native to the interrogated cell, and viral RNA or DNA present in the interrogated cell. In a preferred embodiment of the tracking method aspect of invention, the target nucleic acid is a native mRNA or a single-stranded viral RNA in the interrogated cell.

Oligonucleotide Probe Design and Synthesis

The basic principles of oligonucleotide design, synthesis and use are well known. Those basic principles apply generally to the design, synthesis and use of the oligonucleotide probes used in this invention.

This invention includes embodiments comprising an essentially unlimited number of different oligonucleotide probes. For example, an oligonucleotide used in this invention can vary considerably in length. The preferred length will depend on considerations such as interrogated cell type, method of probe introduction into the interrogated cell, probe concentration used, target nucleic acid length, target nucleic acid copy number, target nucleic acid G-C content, and interrogated cell temperature. Preferably the length of the oligonucleotide probe used in this invention is from 10 to 200 nucleotides. More preferably, the length is from 10 to 100 nucleotides. Most preferably it is from 15 to 50 nucleotides. For a general discussion of oligonucleotide probe length and factors relating thereto, see: Goodchild, "Inhibition of Gene Expression by Oligonucleotides," in *Topics in Molecular and Structural Biology, Vol. 12: Oligodeoxynucleotides* (Cohen, ed.), MacMillan Press, London, pp. 53–77.

Regardless of oligonucleotide probe length, the probe can vary in nucleotide sequence. The nucleotide sequence of an oligonucleotide probe used in this invention will depend on the sequence of the target nucleic acid. The probe's nucleotide sequence must have sufficient complementarity to the target nucleic acid to allow probe hybridization with the target nucleic acid, under conditions inside the interrogated cell. Preferably, base pair matching between the probe and target nucleic acid is at least 80%. More preferably, the base pair matching is approximately 100%.

Methods of synthesizing DNA generally, including oligonucleotide probes used in this invention, are well known. For a general discussion of oligonucleotide synthesis, see Caruthers, "Synthesis of oligonucleotides and Oligonucleotide Analogs," in *Topics in Molecular and Structural Biology, Vol. 12: oligodeoxynucleotides* (Cohen, ed.), MacMillan Press, London, pp. 9–24. Apparatuses for automated DNA synthesis are commercially available. Preferably automated DNA synthesis is employed in obtaining oligos used in the practice of this invention.

Typically, a caged fluorochrome-labeled, oligonucleotide probe used in this invention is obtained in a two step process. The first step is synthesis of an oligonucleotide that includes a modified base at each position in its sequence where a caged fluorochrome moiety is desired. The second step is covalent attachment of the caged fluorochrome to the modified base.

The purpose of the modified base used in the first step is to provide a functional group through which the caged fluorochrome is covalently attached to the oligonucleotide, in the second step. Preferably, the functional group provided by the modified base is a primary amino group. Preferably, the functional group is at the end of a spacer arm.

During synthesis of an oligonucleotide, the functional group provided by the modified base (for attachment of the caged fluorochrome moiety) typically bears a protecting (blocking) group, e.g., a trifluoroacetamide group. One of skill in the art will recognize that the protecting group must be removed by a suitable chemical reaction before the functional group can be used for attachment of the caged fluorochrome moiety.

Figure 3A:
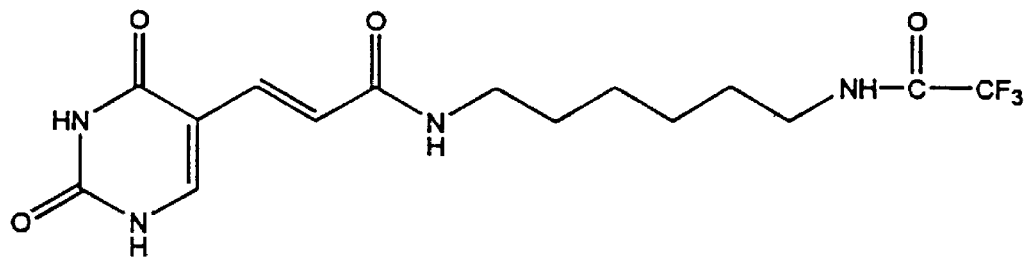
FIG. 3A is the chemical formula of a preferred modified base.
Figure 3B:
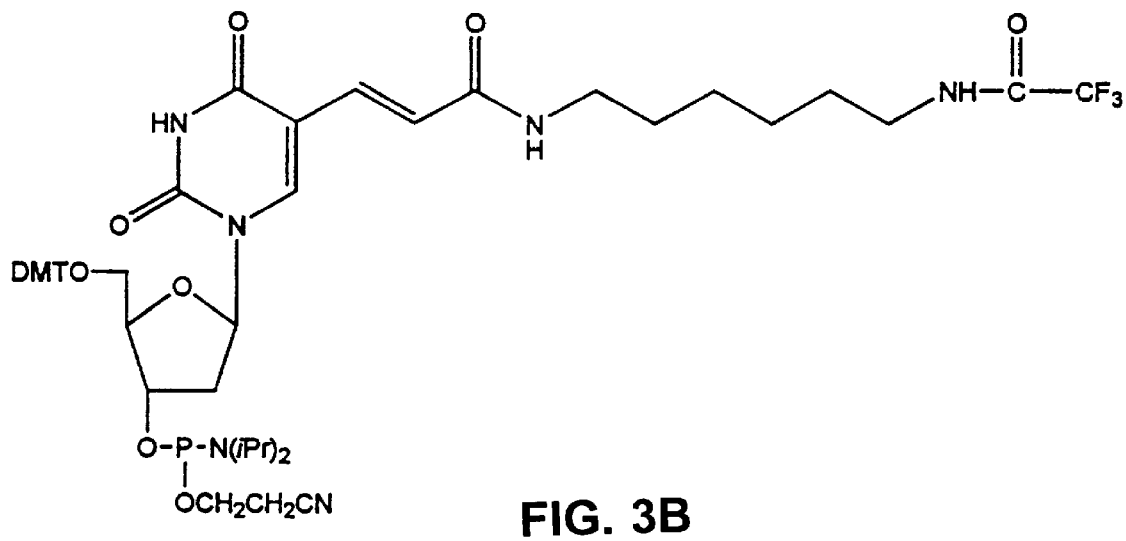
FIG. 3B is the chemical formula of a preferred deoxynucleotide (dT) analog comprising the modified base of FIG. 3A.

For preparation of amino modified bases, see Jablonski et al. ((1986) *Nucleic Acids Res.* 14:6115–6128) and Ruth ((1984) *DNA* 3:123). A particularly preferred modified base is a thymine analog with the chemical structure shown in FIG. 3A. The thymine analog depicted in FIG. 3A can be conveniently incorporated into an oligo by means of a dT analog whose structure is shown in FIG. 3B. The dT analog depicted in FIG. 3B is available commercially as "Amino-Modifier C6 dT" (Glen Research, Sterling, Va.). "Amino-Modifier C6 dT" is designed for use in conventional automated DNA synthesis. The trifluoroacetamide group on "Amino-Modifier C6 dT" is a protecting group. It is removed by hydrolysis during deprotection, to expose a primary amine group for use in attachment of a caged fluorochrome moiety.

The total number, and the spacing, of the modified bases (and covalently attached caged fluorochrome moieties) in the oligonucleotide can vary, in the practice of this invention. Preferably, a modified base is incorporated at approximately every tenth base position in the nucleotide sequence of the probe. Incorporation of modified bases, and thus caged fluorochrome moieties, closer than every ten bases causes quenching of fluorescence and concomitant loss of visual signal strength.

Attachment of Caged Fluorochrome Moieties to Oligonucleotides

Numerous caged fluorochromes are known. Any caged fluorochrome that can be attached to a suitable probe can be used in the practice of this invention. Preferred fluorochromes are those with a succinimidyl ester moiety, which can be used for covalent linkage to an oligonucleotide probe through a primary amine on a modified base. Examples of such preferred caged fluorochromes are: Rhodamine Green™ bis-(((4,5-dimethoxy-2-nitrobenzyl)oxy)carbonyl) -caged succinimidyl ester (NVOC-caged Rhodamine Green™ SE), and Rhodamine Green™ bis-(((4,5-dimethoxy-2-nitrobenzyl)oxy)carbonyl)-caged sulfosuccinimidyl ester (NVOC-caged Rhodamine Green™ SSE), which are both commercially available (Molecular Probes, Inc., Eugene, Oreg.). Another preferred caged fluorochrome is biscaged carboxyfluorescein ("C2CF"), whose preparation is described by Mitchison (*J. Cell Biol.* 109:637–652 (1989).

In a preferred method of making oligonucleotide probes for use in this invention, C2CF, NVOC-caged Rhodamine Green™ SE, or NVOC-caged Rhodamine Green™ SSE is allowed to react with the primary amino group of a modified base. For methods of attaching fluorochromes onto amino groups, see Agrawal et al. (1986) *Nucleic Acids Res.* 14:6227–6245.

A preferred protocol for covalent attachment caged fluorochrome-succinimidyl ester compound to the primary amino group of a modified base is as follows:

1. Dissolve 0.1 µmole of amino-modified oligonucleotide (i.e., 0.1 µmole of free primary amines) in 160 µl of sterile water.
2. Add 20 µl of 10X buffer (0.1M carbonate, pH 9.0).
3. Freshly prepare a 50 mg/ml solution of caged fluorochrome-succinimidyl ester compound in DMSO. Add 20 µl of the solution to the reaction mixture.
4. Add DMSO up to one half total volume to solubilize any precipitate that forms.
5. Allow the mixture to stand at least 2 hours. (Note: Overnight reaction may be more convenient.)
6. Purify the reaction mixture on a POLY-PAK™ cartridge (Glen Research), or a column containing SEPHADEX™ G-25 or G-50, to remove the excess label.

Kits containing reagents prepared for this protocol are commercially available (e.g., Glen Research, Sterling, Va.).

In situ Hybridization

In situ hybridization methods are well known in the art. See, e.g., Singer et al., "Optimization of in situ hybridization using isotopic and nonisotopic detection methods," *Biotechniques* 4:230–250 (1986).

Introduction of Probe into Interrogated Living Cell

A caged fluorochrome-labeled oligonucleotide probe used according to this invention can be introduced into an interrogated living cell by any suitable method. Numerous methods for introducing DNA, including synthetic oligonucleotides, into living cells are known in the art. For a general discussion of cellular uptake of antisense oligos, see Akhtar et al. (1992) Trends in Cell Biology 2:139–144.

The preferred method for introducing caged fluorochrome labeled oligonucleotide probes into target cells in the practice of this invention will depend on various factors, including the type of cell to be interrogated, e.g., animal, plant, or bacterial. Selection of methods suitable for introducing probes into cells of a particular type is within ordinary skill in the art.

Cells can take up naked DNA. Oligonucleotides have been shown to be passively taken up by cultured cells following addition of naked oligonucleotides to the culture medium (e.g., at a concentration in the range of 10–200 $\mu$M). Additional methods for introducing oligos into target cells include the following: liposome mediated delivery; microinjection (see, e.g., Leonetti et al. (1991) Proc. Natl. Acad. Sci. USA 88:2702–2706); electroporation (see, e.g., Sambrook et al., Molecular Cloning—A Laboratory Manual (2d Ed.), Cold Spring Harbor Laboratory Press (1989), at pages 16.54–16.55); bombardment with high velocity tungsten microprojectiles (see, e.g., BioRad Technical Bulletin #1687, BioRad, Hercules, Calif.; Johnston (1990) Nature 346:776); transfection of coprecipitates of calcium phosphate and DNA (see, e.g., Sambrook et al., supra, at pages 16.32–16.40); and transfection mediated by DEAE-dextran (see, e.g., Sambrook et al., supra, at pages 16.41–16.46).

Fluorescence Microscopy and Interrogation of Living Cells

Living cells are preferably interrogated in a suitable culture medium on an inverted fluorescence microscope. Preferably, a heated stage is used to maintain the cells at a suitable temperature. The composition of a suitable medium and a suitable stage temperature will depend on the type of cell being viewed, and can be readily determined by one of ordinary skill in the art. For long observation times involving cultured mammalian cells, the microscope is chambered in 5% $CO_2$ to maintain cell viability.

An advantageous feature of the present invention is that fluorochrome uncaging can be done throughout the volume of a cell to be interrogated, or in only a small part of the cell. The extent of the cell volume exposed to the uncaging light is determined by the design of the uncaging light beam. In a preferred method of uncaging, the uncaging light beam is a laser beam approximately 0.5 $\mu$m in diameter. Because uncaging occurs in three dimensions, a 0.5 $\mu$m beam uncages fluorochromes in a 0.5 $\mu$m cylindrical section through the cell. Fluorochromes on probes within that cylindrical section, and only those fluorochromes, immediately become fluorescent, and thus can be detected and tracked over time.

Preferably, uncaging is achieved with an exposure time of about 1 to about 50 msec. Intensity of the uncaging light is adjusted accordingly. of course, the uncaging light must not have an intensity great enough to cause significant damage to the living cell being interrogated. Low doses of 365 nm light do not measurably affect cell viability or growth.

Uncaged probes that are hybridized do not exhibit significant translocation over time periods as short as a few seconds. Nonhybridized, uncaged probes are distinguishable, because they rapidly translocate through diffusion, as a result of their relatively small size. This rapid diffusion effectively dilutes concentration of fluorescence signals and allows hybridized uncaged probes to be identified and tracked.

FIGS. 1A–1F demonstrate the use of digital imaging fluorescence microscopy according to the present invention, to track poly(A)+mRNA molecules moving in a living L6 cell. A caged fluorescein-labeled oligo dT probe was introduced into L6 cells using Tfx™-50 Reagent (Promega, Madison, Wis.) according to the vendor's recommended protocol. Twenty-one 0.5 $\mu$m optical sections (50 msec./section) were taken through the z-plane of the cell, and automatically captured on a high resolution, high sensitivity CCD camera. Each image shown in FIGS. 1A–1F is the same plane.

Figure 1B:
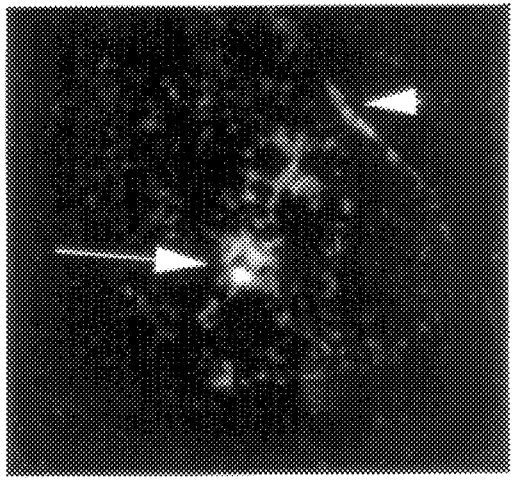
FIG. 1B is a digital image of a living cell 700 milliseconds after uncaging of a caged fluorochrome-labeled oligo-dT probe, after the autofluorescence background has been electronically subtracted. The probe was uncaged with a UV laser ($\lambda$=360 nm) beam approximately 0.5 $\mu$m in diameter.
Figure 1C:
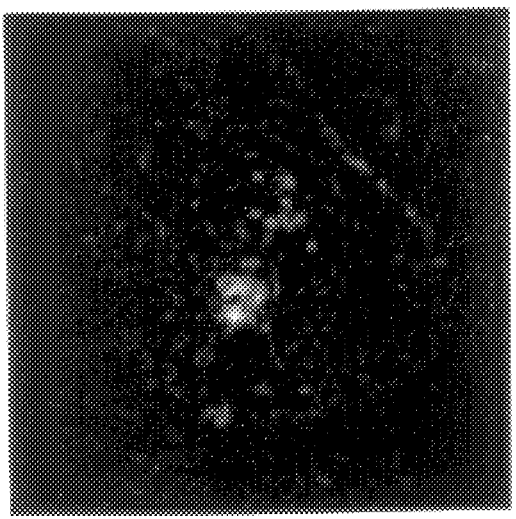
FIG. 1C is the same as FIG. 1B, except that the image was taken 10 seconds after uncaging.
Figure 1D:
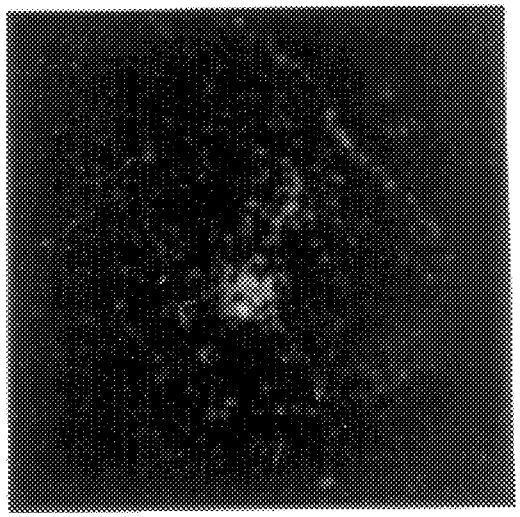
FIG. 1D is the same as FIGS. 1B and 1C, except that the image was taken 20 seconds after uncaging.
Figure 1E:
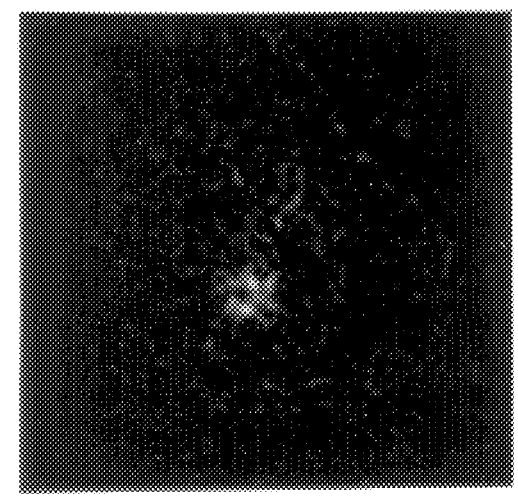
FIG. 1E is the same as FIGS. 1B–1D, except that the image was taken 30 seconds after uncaging.

The uncaging area is the approximately 0.5 $\mu$m bright spot indicated by the tailed arrow (FIG. 1B). In this experiment, a portion of the labeled probe population moved to an area of the nuclear envelope indicated by the arrowhead, within 700 milliseconds (FIG. 1B).

Figure 1F:
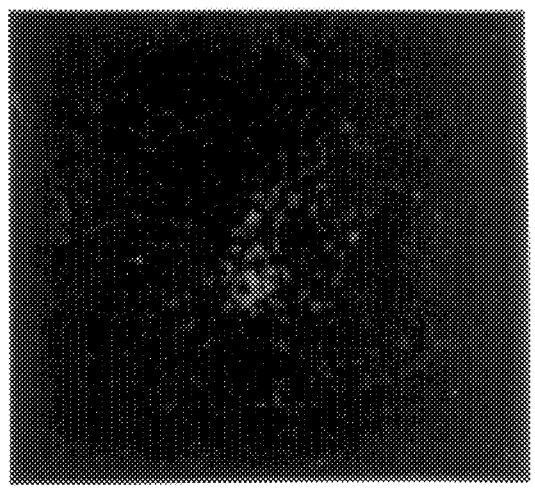
FIG. 1F is the same as FIGS. 1B–1E, except that the image was taken 50 seconds after uncaging.

FIG. 1A is a digital image before uncaging of a cage fluorochrome-labeled oligo-dT probe (after subtraction of autofluorescence background). FIGS. 1B–1F are digital images representing a 50-second time course after uncaging of the caged probe. Time intervals are 700 milliseconds (FIG. 1B); 10 seconds (FIG. 1C); 20 seconds (FIG. 1D); 30 seconds (FIG. 1E); and 50 seconds (FIG. 1F).

Digital Imaging Fluorescence Microscopy and Data Analysis

Digital imaging fluorescence microscopy is known in the art. Complete digital imaging fluorescence microscopy systems, or components for assembly of a complete system, are commercially available. Digital imaging fluorescence microscopy and data analysis are described below essentially as described in Singer et al., U.S. application Ser. No. 08/546,072.

A basic digital imaging fluorescence microscopy system includes the following operationally linked components: (1) a conventional fluorescence microscope, (2) a means for optical sectioning, e.g., a micrometer, (3) an optical detector, e.g., a CCD camera, and (4) a digital computer to store optical data. The foregoing basic components are commercially available. The operational linkage of the basic components is within ordinary skill in the art. Moreover, complete digital imaging fluorescence microscopy systems are commercially available (Scanalytics, Billerica, Mass.).

Methods and published software for data analyses carried out in the practice of the present invention are known in the art. A preferred software package is known as Data Analysis and Visualization Environment ("DAVE") Release 0.7 (May 18, 1994). DAVE was written by Jeff Collins and Lawrence M. Lifshitz and has been published by the University of Massachusetts Medical School.

Basic references on digital image processing include the following: John C. Russ, The Image Processing Handbook, 2d ed., CRC Press, Boca Raton, Fla., (1995); and Kenneth R. Castleman, Digital Image Processing, Prentice-Hall, Inc., Englewood Cliffs, N.J., (1979).

Preferably, the present invention is practiced using a highly sensitive charge-coupled device (CCD) camera to collect light from a fluorescence microscope. The collected light is typically recorded as a series of optical sections from a sample. Much of the light in any given optical section is out-of-focus light that has spread from numerous individual point sources. Therefore, an unprocessed optical section is inevitably convoluted, and image resolution is diminished accordingly.

Using a standard 3D image restoration algorithm known as exhaustive photon reassignment ("EPR"), a restored (i.e., deconvoluted) image can be generated from a series of optical sections. EPR reassigns all of the collected light in a series of optical sections to the original point sources of the light. Fluorescent beads placed in the imaged sample are used to obtain a "point spread function," which is used in the EPR algorithm.

Determination of Point Spread Function

The optical parameters for a microscope can be described in terms of the direct-space point spread function ("PSF"). Principles and procedures relating to PSF are within ordinary skill in the art.

One approach to determining the PSF of a microscope is to directly image single fluorescent beads with a diameter of 0.1 micrometer. Since this diameter is smaller than the resolution limit, the beads effectively behave as point objects. For a discussion of PSF in digital imaging fluorescence microscopy, see, e.g., Hiraoka et al., *Science* 238:36–41 (1987).

In addition to enhancing resolution, EPR enhances the sensitivity of detection, because it utilizes all of the light collected. This is in contrast to confocal methods, where a significant fraction of the light signal is never received by the detector.

Exhaustive Photon Reassignment (EPR)

EPR is a standard mathematical technique used to generate a restored image from a series of optical sections. EPR is described by Carrington et al. in U.S. Pat. No. 5,047,968. EPR can be carried out on a conventional computer system, using commercially available software (Scanalytics, Billerica, Mass.).

Experimental Example

In situ Hybridization of Beta-Actin mRNA

In situ Hybridization

Immediately before hybridization, cells were permeabilized for 5 minutes in 0.5% TRITON™ in PBS and washed in 2xSSC for 5 to 10 minutes. Beta-actin mRNAs were detected by a single step in situ hybridization technique using synthetic 50–53 mer, approximately 50% GC rich, synthetic DNA oligomer probes specific to sequences of the 3' untranslated region (3' UTR) and coding region of rat beta-actin mRNA.

Five oligonucleotide probes of equal length, complementary to five non-overlapping regions of the 3' UTR of beta actin were synthesized.

Three oligonucleotide probes of equal length, complementary to the coding regions of the beta-actin gene were also synthesized. Various combinations of these probes were used to detect actin mRNAs. These probes were chemically linked to caged fluorescein through modified thymidine residues at every ten base positions.

Twenty nanograms each of the beta-actin 3'-UTR and coding region probes, and 20 micrograms each of sonicated salmon sperm and *E. coli* tRNA were combined in a 1.5 ml Eppendorf tube, dried down in a SPEEDVAC®, and subsequently taken up in 10 microliters of 100% formamide. This solution was heated at 90° C. for 2 minutes and then diluted with 10 microliters of hybridization buffer containing 1:2:2 of BSA (Boehringher Manneheim 20 mg/ml), 20x SSC and water. The resulting hybridization mixture of 50% formamide and 0.6M sodium was placed on parafilm, immediately covered with a coverslip and incubated at 37° C. in a humidified incubator in the dark for 3.5 to 4.0 hours.

Each coverslip was then washed in 3 ml of 50% formamide and 2x SSC (0.3M sodium) for 0.5 hour at 37° C., and 2 times in 3 ml of 1x SSC for 15 minutes, and mounted on slides in a mounting medium. A preferred mounting medium includes phenylenediamine for its antioxidant properties, which properties advantageously prevent or retard photobleaching. The coverslip was sealed with clear nail polish and subsequently stored at 4° C.

Digital Imaging Fluorescence Microscopy

A digital imaging microscope system comprising a Nikon DIAPHOT™ inverted epifluorescence microscope modified to collect images under computer control was used to collect digitized optical sections, which were used to generate 3D images of fluorescent probes in cells. The samples were illuminated with a mercury lamp, using dichroic filters for excitation, and emission wavelengths of 485 nm and 530 nm, respectively, for fluorescein. Light was collected with a Nikon 60x planapochromat objective with a numerical aperture of 1.4 combined with a 2.5x or 5.0x photo eyepiece. Collected light was detected with a cooled CCD camera (Photometrics Inc., Tucson, Ariz.). Pixel diameter was 20 micrometers. Dynamic range was 1:16383 (14 bit).

A series of 20–30 optical sections were first acquired on a caged cell, using 0.25 or 0.10 micrometer intervals, with a 3000 to 4000 millisec exposure time for fluorescein, per interval.

The entire cell was then exposed to UV light through a DAPI filter set for 2–5 minutes. The UV transmissivity of objective lenses varies. Therefore, the amount of UV exposure is adjusted to give total uncaging. Preferred objectives are 100x Zeiss planapo, NA 1.3 (2 min. uncaging time), or 40x Nikon planapo, NA 1.3 (5 min. uncaging time). If an objective is being used that does not transmit UV light well, e.g., 60x Nikon planapo, NA 1.4, the objective can be changed for the uncaging step. After uncaging, the fluorescence present in the uncaged cell was recorded by taking optical sections identical to those obtained on the caged cell.

Fluorescein-labeled beads with a diameter of 200 nm were mounted on separate slides, but in an aliquot of the same mounting media used for the cells, and were optically sectioned, (50 or 60 optical sections) at 0.25 or 0.10 micrometer intervals. The resulting bead images were used to determine the fluorescein point spread functions of the optical system. The number of optical sections used for the point spread function was at least 2-fold greater than the number of optical sections used for imaging. The resulting point spread function was used in the subsequent EPR 3D image restoration process.

A Silicon Graphics Indigo 2 Graphics Extreme workstation was used for image processing and analysis. Images were restored at 200 to 400 iterations and at alpha values of 0.00001 and 0.000005, respectively. Other commercially available workstations can also be used. For a discussion of image preparation and restoration, see Carrington et al., *Non-Invasive Techniques in Cell Biology*, Foster et al. (eds.), Wiley-Liss, New York (1990), at 53–72.

Quantitative Analysis of Beta-Actin mRNA

The samples of cells subjected to in situ hybridization were imaged by collection of 20 to 30 optical sections per image. Exposure times were 2000 msec for the CY3, and 3000 or 4000 msec per optical section for fluorescein images.

The images were prepared for restoration using standard algorithms that subtract dark current and background and normalize the image intensities in each optical section to the total intensity of the first optical section. Normalization to the first optical section corrects photobleaching effects in the subsequent sections. The prepared images were processed using EPR, a known restoration algorithm which reassigns the collected light from each optical section to its original point source. The restoration is carried out using 200 to 400 iterations and an alpha value of 0.00001 or 0.000005, respectively. That accomplished 0.003 convergence to discrete point sources.

Next, the numerical value of the fluorescence present in each pixel of the pre-uncaging restored image was subtracted from the fluorescence measured in each pixel in the same cell after uncaging.

Using caged fluorochromes according to the present invention offers a distinct advantage over the prior art method. The specific background and autofluorescence present in each pixel of the cell image is subtracted from the fluorescence measured in the same pixel after uncaging. This markedly improves the sensitivity of detection for in situ hybridization in a unique way, because fluorescence is not approximated through an average value. The actual value is measured and subtracted, on a pixel-by-pixel basis. Therefore, the signal remaining in any given pixel is a pure signal.

The restored images were then imported into the Data Analysis and Visualization Environment (DAVE) and visually analyzed to determine the spatial distribution of the signal.

Probes Directed to External Target Molecules in Flow Cytometry

Flow cytometry according to the present invention can be performed on cells that have taken up a caged fluorochrome-labeled probe directed to an intracellular target. Typically, however, flow cytometry according to the invention will involve a caged fluorochrome-labeled probe for an external target molecule that distinguishes the cells of interest from surrounding cells. For example, the external target molecule can be a membrane-bound receptor protein. In that situation, the caged fluorochrome-labeled probe can be a polypeptide ligand or an antibody (immunoglobulin) specific for the receptor protein.

Methods for covalently linking caged fluorochromes to polypeptides, including immunoglobulins, are generally the same as methods for covalently linking conventional fluorochromes. Those methods are known to those of ordinary skill in the art. See, e.g., Cebra et al., *Immunology* 95:230 (1965).

Fluorochrome-Uncaging Flow Cytometer

The basic principles of flow cytometry, and the design and construction of flow cytometers, are known to those of ordinary skill in the art, and therefore are not repeated here. See, e.g., H. M. Shapiro, *Practical Flow Cytometry*, Third Edition, Alan R. Liss, Inc., New York (1995). Flow cytometers intended for research or clinical use, or both, are commercially available. Examples of commercial flow cytometers include the Becton Dickinson FACStar™ instruments and the Coulter EPICS™ instruments.

The invention provides a fluorochrome-uncaging flow cytometer that sorts cells using a non-probabilistic method. The following discussion refers to FIG. 2, which is a schematic diagram of a flow system 30 in a fluorochrome-uncaging flow cytometer according to the present invention. The conventional features of the device will be discussed first.

Figure 2:
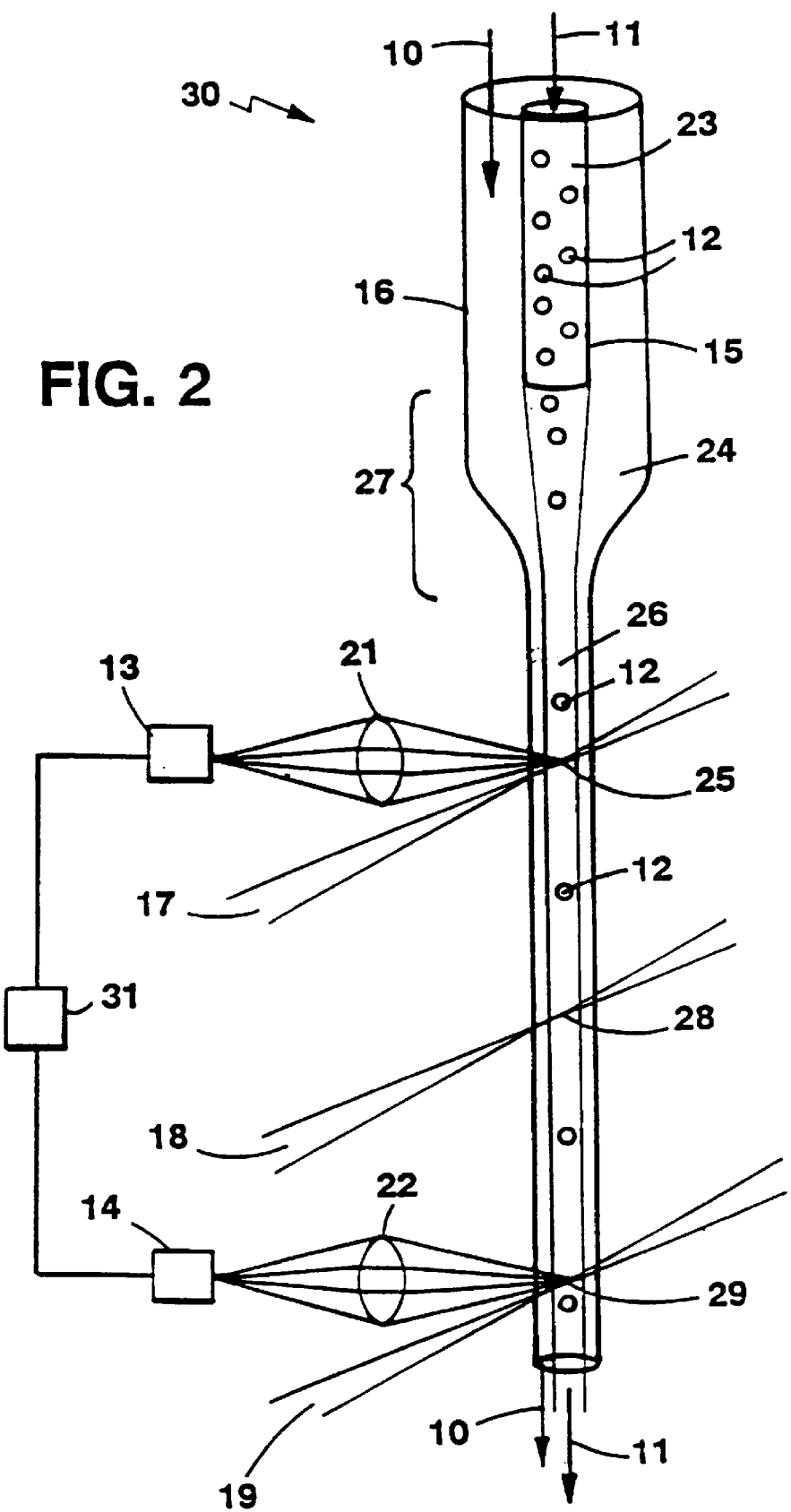
FIG. 2 is a schematic diagram of a flow system in a fluorochrome-uncaging flow cytometer.

A single file flow of cells 12 is produced from a core stream 11, consisting of a core fluid 23 and sample cells 12. The core stream 11 flows into a core injector 15, which connects to a core neck-down region 27, which tapers down to a core 26. The core diameter is selected so as to force a single file flow of cells without clogging. A wider, coaxial capillary 16 surrounds the core injector 15, core neck-down region 27, and core 26. A sheath stream 10, consisting of a cell-free sheath fluid 24 surrounds the core 26. Preferably, the core stream and sheath stream flow downward, as illustrated in FIG. 2. One of ordinary skill in the art will recognize, however, that the flow can also be horizontal or upward.

A conventional fluorescence-activated flow cytometer includes a first fluorescence excitation light beam 17, focused on a first interrogation point 25 in the core 26. Sample cells 12 are interrogated as they pass the first interrogation point 25. The conventional device also includes a first collection lens 21 which collects fluorescence emitted from interrogated sample cells and focuses the collected light onto a first photodetector 13.

The fluorochrome-uncaging flow cytometer of the present invention includes an uncaging light beam 18 focused on an uncaging point 28 in the core, which uncaging point 28 is downstream from the first interrogation point 25. The flow cytometer of the invention also includes a second fluorescence excitation light beam 19, focused on a second interrogation point 29 in the core 26. The second interrogation point 29 is downstream from the uncaging point 28.

In the fluorochrome-uncaging flow cytometer, the first and second fluorescence excitation light beams 17, 19 have the same wavelength and the same intensity. Two separate sources can be used for the first and second excitation beams, and then calibrated to match each other as closely as possible. Preferably, however, the first and second excitation light beams 17, 19 are obtained by means of a beam-splitter and a single source. The design and construction of suitable splitting optic systems are within ordinary skill in the art. Preferably, both excitation light beams 17, 19 and the uncaging light beam 18 are laser beams.

Preferably, the excitation light beams 17, 18, and 19 are focused on the core with a beam diameter equivalent to, or slightly greater than, the core diameter. This ensures that substantially the entire volume of every cell in the core stream will be exposed to each of the three light beams.

Typically, the uncaging light beam 18 is in the ultraviolet portion of the spectrum, and the excitation light beams 17, 19 and the fluorescent emissions are in the visible portion of the spectrum. Therefore, the coaxial capillary 16 and the core 26 are preferably made of a material that is transparent to both visible and ultraviolet light, e.g., quartz.

The first and second photodetectors 13, 14 are operably linked to an electronic data system 31. Upon interrogation of a cell at the first interrogation point 25, the data system 31 stores a value for total fluorescence from the cell, i.e., before uncaging of the caged fluorochrome. This is the total autofluorescence value for the cell. Upon interrogation of the cell at the second interrogation point 29, the data system 31 stores a second value for total fluorescence from the cell, i.e., after uncaging of the caged fluorochrome. This is the probe fluorescence-plus-autofluorescence for the cell. The data system then subtracts the autofluorescence value from the probe fluorescence-plus-autofluorescence value. By subtracting the autofluorescence background, the improved flow cytometer obtains a fluorescence measurement that represents essentially pure signal from the caged fluorochrome-labeled probe. The fluorochrome-uncaging flow cytometer repeats this process for each cell passing through the flow system.

Other embodiments are within the following claims.

We claim:

1. A method for removing autofluorescence background from a fluorescent in situ hybridization image of cellular material, the method comprising the steps of:

(a) fixing said cellular material with a fixative that retains and preserves a target molecule, if present, in said cellular material;

(b) contacting said cellular material with a molecular probe that binds specifically to said target molecule, said molecular probe being labeled with a caged fluorochrome;

(c) interrogating said cellular material a first time, to produce a first digitized image including an autofluorescence background;

(d) uncaging the fluorochrome label on said molecular probe;

(e) interrogating said cellular material a second time to produce a second digitized image including (1) a fluorescence signal from the uncaged fluorochrome on said molecular probe, and (2) said autofluorescence background; and (f) digitally subtracting said first digitized image from said second digitized image, thereby removing autofluorescence background from the fluorescent in situ hybridization image.

2. The method of claim 1, wherein said first digitized image is subtracted from said second digitized image on a pixel-by-pixel basis.

3. The method of claim 1, wherein said cellular material includes a cell nucleus.

4. The method of claim 3, wherein said target molecule is a nucleic acid and said molecular probe is an oligonucleotide.

5. The method of claim 1, wherein said caged fluorochrome is selected from the group consisting of bis-caged carboxyfluorescein, Rhodamine Green™ bis-(((4,5-dimethoxy-2-nitrobenzyl)oxy)carbonyl)-caged succinimidyl ester, and Rhodamine Green™ bis-(((4,5-dimethoxy-2-nitrobenzyl)oxy)carbonyl)-caged sulfo-succinimidyl ester.

6. A method for tracking a target molecule in a living cell, said method comprising the steps of:

(a) obtaining a molecular probe that binds specifically to said target molecule, said molecular probe being labeled with a caged fluorochrome;

(b) introducing said molecular probe into said living cell;

(c) interrogating said living cell a first time, to produce a first digitized image including an autofluorescence background;

(d) uncaging said fluorochrome in a portion of said living cell;

(e) interrogating said cell a second time to produce a second digitized image including (1) a fluorescence signal from the uncaged fluorochrome on said molecular probe, and (2) said autofluorescence background;

(f) digitally subtracting said first digitized image from said second digitized image, thereby obtaining a substantially autofluorescence-free digitized image;

(g) repeating steps (c)–(f) at selected time intervals; and (h) comparing the substantially autofluorescence-free digitized images obtained at said selected time intervals, to detect a slow-moving fluorescence signal, as an indication of said probe molecule bound to said target molecule, thereby tracking said target molecule in a living cell.

7. The method of claim 6, wherein said first digitized image is subtracted from said second digitized image on a pixel-by-pixel basis.

8. The method of claim 6, wherein said portion of said cell is the entire cell.

9. The method of claim 6, wherein said portion of said cell is less than the entire cell.

10. The method of claim 6, wherein said fluorochrome is uncaged by means of a laser beam having a diameter from about 0.1 $\mu$m to about 2.0 $\mu$m.

11. The method of claim 10, wherein said diameter is about 0.5 $\mu$m.

12. The method of claim 6, wherein said caged fluorochrome is selected from the group consisting of bis-caged carboxyfluorescein, Rhodamine Green™ bis-(((4,5-dimethoxy-2-nitrobenzyl)oxy)carbonyl)-caged succinimidyl ester, and Rhodamine Green™ bis-(((4,5-dimethoxy-2-nitrobenzyl)oxy)carbonyl)-caged sulfo-succinimidyl ester.

13. A fluorochrome-uncaging flow cytometer comprising an electronic data system and a flow system, said flow system comprising:

(a) a core through which cells pass single file;

(b) a first fluorescence excitation light beam focused on a first fluorescence interrogation point in said core;

(c) a first collection lens situated so as to collect fluorescence emitted from said first fluorescence interrogation point and focus said fluorescence onto a first photodetector operably linked to said data system;

(d) an uncaging light beam focused on an uncaging point in said core, said uncaging point being downstream from said first interrogation point;

(e) a second fluorescence excitation light beam focused on a second fluorescence interrogation point in said core; and (f) a second collection lens situated to collect fluorescence emitted from said second fluorescence interrogation point and focus said fluorescence onto a second photodetector operably linked to said data system.

14. The fluorochrome-uncaging flow cytometer of claim 13, wherein said first fluorescence excitation light beam or said second fluorescence excitation light beam is a laser beam.

15. The fluorochrome-uncaging flow cytometer of claim 13, wherein said uncaging light beam is a laser beam.

16. The fluorochrome-uncaging flow cytometer of claim 13, wherein said uncaging light beam has a wavelength in the ultraviolet portion of the electromagnetic spectrum.

17. A non-probabilistic method for obtaining a fluorescence signal value in fluorescence-based flow cytometry of cells in a cell population contacted with a caged fluorochrome-labeled molecular probe that binds specifically to a target molecule, said method comprising the following steps:

(a) moving said cells single file into a core in a fluorochrome-uncaging flow cytometer;

(b) moving a first cell through a excitation light beam focused on a first interrogation point in said core, in a first interrogation;

(b) collecting fluorescence emitted from said first cell in response to said first interrogation, and focusing the collected fluorescence onto a first photodetector operably linked to an electronic data system;

(c) storing an autofluorescence background value from said first photodetector in said electronic data system;

(d) moving said first cell through an uncaging light beam focused on an uncaging point in said core, said uncaging point being downstream from said first interrogation point in said core;

(e) moving said first cell through a second excitation light beam focused on a second interrogation point in said core, in a second interrogation;

(f) collecting fluorescence emitted from said first cell in response to said second interrogation, and focusing the collected fluorescence onto a second photodetector operably linked to the electronic data system;

(g) storing an autofluorescence background-plus-signal value from said second photodetector, in said electronic data system; and (h) subtracting said autofluorescence background value from said autofluorescence background-plus-signal value, thereby obtaining a fluorescence signal value.

18. The method of claim 17, wherein said excitation light beam focused on said first interrogation point, or said excitation light beam focused on said second interrogation point, is a laser beam.

19. The method of claim 17, wherein said uncaging light beam is a laser beam.

20. The method of claim 17, wherein said uncaging light beam has a wavelength in the ultraviolet portion of the electromagnetic spectrum.

* * * * *